(12) United States Patent
Devonald et al.

(10) Patent No.: US 10,761,103 B2
(45) Date of Patent: Sep. 1, 2020

(54) BIOMARKERS RELATED TO KIDNEY FUNCTION AND METHODS INVOLVING THEIR USE

(71) Applicants: NOTTINGHAM UNIVERSITY HOSPITALS NHS TRUST, Nottingham, Nottinghamshire (GB); THE UNIVERSITY OF NOTTINGHAM, Nottingham, Nottinghamshire (GB)

(72) Inventors: Mark Devonald, Nottingham (GB); David Gardner, Nottingham (GB)

(73) Assignees: THE UNIVERSITY OF NOTTINGHAM, Nottingham (GB); NOTTINGHAM UNIVERSITY HOSPITALS NHS TRUST, Nottingham (GB)

( * ) Notice: Subject to any disclaimer, the term of this patent is extended or adjusted under 35 U.S.C. 154(b) by 73 days.

(21) Appl. No.: 15/541,980

(22) PCT Filed: Jan. 7, 2016

(86) PCT No.: PCT/GB2016/050028
§ 371 (c)(1),
(2) Date: Jul. 6, 2017

(87) PCT Pub. No.: WO2016/110701
PCT Pub. Date: Jul. 14, 2016

(65) Prior Publication Data
US 2018/0017581 A1    Jan. 18, 2018

(30) Foreign Application Priority Data

Jan. 7, 2015 (GB) .................................. 1500200.9

(51) Int. Cl.
G01N 33/50 (2006.01)
G01N 33/84 (2006.01)
G01N 33/68 (2006.01)
G01N 21/64 (2006.01)

(52) U.S. Cl.
CPC ......... G01N 33/84 (2013.01); G01N 33/6893 (2013.01); G01N 33/6896 (2013.01); *G01N 21/648* (2013.01); *G01N 2800/085* (2013.01); *G01N 2800/347* (2013.01)

(58) Field of Classification Search
CPC .................... G01N 2800/085; G01N 2800/347
See application file for complete search history.

(56) References Cited

U.S. PATENT DOCUMENTS

2013/0217637 A1* 8/2013 Barasch ................. C07K 14/47
514/21.2

FOREIGN PATENT DOCUMENTS

| WO | 2000/065346 A1 | 11/2000 |
| WO | 2003/077901 A1 | 9/2003 |
| WO | 2006/017650 A2 | 2/2006 |
| WO | 2008/066862 A2 | 6/2008 |
| WO | 2009/039298 A2 | 3/2009 |
| WO | 2010/057184 A2 | 5/2010 |

OTHER PUBLICATIONS

Von Bonsdorff, Leni et al. "Bleomycin-detectable iron assay for non-transferrin-bound iron in hematologic malignancies." Clinical Chemistry (2002) 48 307-314. (Year: 2002).*
Pennemans, Valerie et al. "The association between urinary kidney injury molecule 1 and urinary cadmium in elderly during long-term, low-dose cadmium exposure: a pilot study." Environmental Health (2011) 10 77. (Year: 2011).*
Reddy, Ramlinga et al. "A correlative study of copper, ceruloplasmin and iron in urine as biomarkers for diabetic nephropathy." International Journal of Biochemistry (2013) 108 207-211. (Year: 2013).*
International Search Report and Written Opinion for corresponding Application No. PCT/GB2016/050028 (dated Mar. 8, 2016).
Akrawinthawong et al., "Urine Catalytic Iron and Neutrophil Gelatinase-Associated Lipocalin as Companion Early Markers of Acute Kidney Injury after Cardiac Surgery: A Prospective Pilot Study," Cardioren. Med. 3(1):7-16 (2013).

* cited by examiner

*Primary Examiner* — Christopher Adam Hixson
(74) *Attorney, Agent, or Firm* — Troutman Pepper Hamilton Sanders LLP (Rochester)

(57) ABSTRACT

The present invention provides a method for diagnosing in a subject Acute Kidney Injury or a related or analogous disease state. The method comprises the steps of a) providing a sample taken from the subject: b) analysing the sample from the subject to determine the level of a biomarker selected from certain atomic species; and c) comparing the level of the biomarker in the sample to a reference level of the biomarker that is characteristic of a healthy subject, eg a subject having normal renal function. An elevated level of the biomarker in the sample relative to the reference level is indicative of Acute Kidney Injury or a related or analogous disease state. The invention also relates to the use of an atomic species selected from those in Table 1 as a biomarker for Acute Kidney Injury or a related or analogous disease state, and test kits comprising an analytical element sensitive to those biomarkers.

14 Claims, 8 Drawing Sheets

BIOMARKERS RELATED TO KIDNEY FUNCTION AND METHODS INVOLVING THEIR USE

This application is a national stage application under 35 U.S.C § 371 of PCT Application No. PCT/GB2016/050028, filed Jan. 7, 2016, which claims the priority benefit of Great Britain Patent Application No. 1500200.9, filed Jan. 7, 2015.

This invention relates to biomarkers related to kidney function, and in particular to biomarkers useful in the diagnosis of Acute Kidney Injury. The invention provides methods involving the detection of such biomarkers, in particular in relation to the diagnosis of acute kidney injury, as well as apparatus and test kits for use in such methods. The methods of the invention may also be useful in relation to certain other disease states.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality.

Acute Kidney Injury (AKI) is a relatively sudden deterioration in renal function, over hours or days (in contrast to a slow decline in renal function over months and years, which is known as chronic kidney disease, CKD). AKI has various causes, the common ones in the hospitalised population being hypovolaemia (dehydration from diarrhoea or vomiting, blood loss from trauma or surgery), ischaemia (reduced blood supply to the kidneys, eg caused by surgery, sudden drop in blood pressure, etc), sepsis (eg as a consequence of a severe infection such as pneumonia) and nephrotoxins (drugs or other substances that are toxic to the kidneys, eg certain types of chemotherapy, antibiotics, and contrast agents used in coronary angiograms and some radiological procedures).

AKI is usually identified by a proportional rise in serum creatinine (SCr) over a defined time. It can also be defined by a fall in hourly urine output, but this is not measured routinely outside intensive care or renal units, so in practice SCr criteria are used. Internationally accepted classification systems have been published to define and stage AKI. There are 3 stages, Stages 1-3, of increasing severity. In a proportion of patients with Stage 3 AKI, "renal replacement therapy" (RRT—either dialysis on the renal unit or haemofiltration on the intensive care unit) might be required, if kidney function is inadequate for safety or survival.

With relatively recent agreement on the definition of AKI, it has become clear that incidence of AKI in the hospitalised population is high, probably 10-20% for any stage of AKI. The inventors have studied incidence and outcomes of AKI locally and have established a local incidence of about 16% of all hospital admissions, which is similar to published studies from other centres internationally.

AKI has a number of important clinical consequences. In particular, AKI is associated with:
a) Significantly increased mortality—both early and late.
b) Increased length of hospital stay: from local data, median length of stay for patients without AKI is 3 days; for those with Stage 1, 2 and 3 AKI it is about 9 days, and for those with Stage '3R' (ie those requiring RRT) it is 22 days.
c) Increased risk of development of chronic kidney disease (CKD), or worsening of pre-existing CKD. CKD itself leads to increased risk of cardiovascular morbidity and mortality.

Moreover, AKI has substantial economic consequences for health service providers. It has been estimated that the marginal costs of AKI to the United Kingdom National Health Service are approximately £450-650 million (around 1 billion $US) per year. Increased length of stay is a major problem for most acute hospitals, with significant cost implications, and the cost of treating increased incidence of CKD is enormous.

AKI is managed poorly in the United Kingdom (National Confidential Enquiry into Patient Outcome and Death, NCE-POD, 'Adding Insult to Injury' 2009). In particular, detection of AKI is poor. A high proportion of cases are either not detected, or are detected late. The report considered that approximately 30% of cases studied were potentially avoidable.

Disease states analogous to AKI may also occur in renal transplantation, which involves significant ischaemic insult to the transplanted kidney. Other organs too, such as the liver, may be subject to analogous forms of injury.

The current standard method of assessing kidney function involves measurement of serum creatinine (SCr), and indeed—as noted above—AKI is defined by specified proportional rise in SCr. However, SCr is acknowledged as a poor marker of kidney injury. SCr levels are indicative of the filtration function of the kidney, rather than of damage to the kidney (which might then lead to reduced filtration function). Moreover, after an insult to the kidney (eg temporary reduction in blood supply during major surgery), SCr probably would not rise for 24 hours or more, even in patients who go on to develop severe AKI (eg those requiring RRT). SCr therefore does not identify those at risk of AKI at a very early stage. SCr is also influenced by many factors such as state of hydration, diet and muscle mass.

In recent years, there has been great interest in the identification of a sensitive and specific biomarker for AKI. An ideal biomarker would be:
a) sensitive and specific;
b) detectable soon after the renal insult;
c) predictive of AKI (and ideally its severity);
d) easy to measure (from blood or urine), involving easy sample preparation and stability in transit to a measuring laboratory, or ideally being measurable in the clinic itself (ie as a 'Point-of-Care Test'); and
e) inexpensive.

Several new putative AKI biomarkers have been reported and developed. Most of the better ones are proteins, measured by ELISA-type tests. To date, however, none has appeared to be clearly superior to others. Examples of biomarkers that have become relatively well established in recent years are:
a. NGAL (Neutrophil Gelatinase Associated Lipocalin): measured in blood or urine; sensitive but not very specific; levels start to rise after 2 hours, and peak at about 4 hours.

b. KIM-1 (Kidney Injury Molecule 1): measured in urine; levels rise later, and peak at about 10 hours after injury; more specific than NGAL.
c. IL-18 (Interleukin 18): measured in urine; rises and peaks later.
d. L-FABP (Liver type fatty acid binding protein).

Since none of these biomarkers is ideal, it has been suggested that specificity and sensitivity might be improved by combining them as a panel of biomarkers, eg NGAL for early sensitive detection, then KIM-1 to increase specificity. Clearly, however, such an approach leads to increased complexity and cost, and does not lead to the desired outcomes of both specificity and rapidity.

There is thus a significant unmet clinical need for a sensitive, accurate, specific and rapid test that provides a reliable indication of the occurrence of AKI.

The inventors have developed a pig model of AKI, and have surprisingly discovered that levels of certain atomic species, present at very low levels in bodily fluids such as urine, rise in urine soon (typically within about one hour) after kidney injury, and then fall to baseline concentrations over the course of several hours. The present invention is based on the use of these atomic species as biomarkers for AKI.

The atomic species useful as biomarkers in accordance with the present invention are generally elements of Periods 3, 4, 5, 6 and 7 of Groups 3-17 of the Periodic Table, as well as the transition metals of the Lanthanide and Actinide series.

A redacted form of the Periodic Table, showing the elements of potential utility in accordance with the present invention is shown in Table 1 below.

TABLE 1

| | Group | | | | | | | | | | | | | | | | | |
|---|---|---|---|---|---|---|---|---|---|---|---|---|---|---|---|---|---|---|
| Period | 1 | 2 | 3 | 4 | 5 | 6 | 7 | 8 | 9 | 10 | 11 | 12 | 13 | 14 | 15 | 16 | 17 | 18 |
| 1 | | | | | | | | | | | | | | | | | | |
| 2 | | | | | | | | | | | | | | | | | | |
| 3 | | | | | | | | | | | | | Al | Si | P | S | Cl | |
| 4 | | | Sc | Ti | V | Cr | Mn | Fe | Co | Ni | Cu | Zn | Ga | Ge | As | Se | Br | |
| 5 | | | Y | Zr | Nb | Mo | Tc | Ru | Rh | Pd | Ag | Cd | In | Sn | Sb | Te | I | |
| 6 | | | | Hf | Ta | W | Re | Os | Ir | Pt | Au | Hg | Tl | Pb | Bi | Po | At | |
| 7 | | | | | | | | | | | | | | Fl | | Lv | | |
| | | | Lanthanides | La | Ce | Pr | Nd | Pm | Sm | Eu | Gd | Tb | Dy | Ho | Er | Tm | Yb | Lu |
| | | | Actinides | Ac | Th | Pa | U | Np | Pu | Am | Cm | Bk | Cf | Es | Fm | Md | No | Lr |

Preferred elements that are of utility in the present invention are transition metals. By "transition metals" is meant in this context any element in the d-block of the Periodic Table, which includes Groups 3 to 12 of the Periodic Table, as well as the f-block Lanthanide and Actinide series, though the latter may be of lesser utility in practice. In this context, "transition metals" also includes the elements zinc, cadmium and mercury that, because they—unlike other transition metals—have no incomplete d-shell in their electronic configuration, are sometimes referred to as "post-transition metals".

Preferred transition metals for use in the present invention are those of Periods 4, 5 and 6 and Groups 3 to 12 of the Periodic Table, ie the elements set out in Table 2:

TABLE 2

| | Group | | | | | | | | | |
|---|---|---|---|---|---|---|---|---|---|---|
| Period | 3 | 4 | 5 | 6 | 7 | 8 | 9 | 10 | 11 | 12 |
| 4 | Sc | Ti | V | Cr | Mn | Fe | Co | Ni | Cu | Zn |
| 5 | Y | Zr | Nb | Mo | Tc | Ru | Rh | Pd | Ag | Cd |
| 6 | | Hf | Ta | W | Re | Os | Ir | Pt | Au | Hg |

Another subset of elements suitable for use in the present invention are those of Periods 4 and 5, and Groups 3 to 17, of the Periodic Table, ie those elements set out in Table 3:

TABLE 3

| | Group | | | | | | | | | | | | | | |
|---|---|---|---|---|---|---|---|---|---|---|---|---|---|---|---|
| Period | 3 | 4 | 5 | 6 | 7 | 8 | 9 | 10 | 11 | 12 | 13 | 14 | 15 | 16 | 17 |
| 4 | Sc | Ti | V | Cr | Mn | Fe | Co | Ni | Cu | Zn | Ga | Ge | As | Se | Br |
| 5 | Y | Zr | Nb | Mo | Tc | Ru | Rh | Pd | Ag | Cd | In | Sn | Sb | Te | I |

Particularly preferred elements for use as biomarkers in accordance with the present invention are those commonly referred to as "heavy metals", which term encompasses any metal or metalloid of environmental concern. Whilst originally used in relation to cadmium, mercury and lead, all of which have harmful effects and are denser than iron, the term is now applied to any other similarly toxic metal or metalloid, regardless of density. Commonly encountered heavy metals that are of utility in the present invention are those set out in Table 4:

TABLE 4

| | |
|---|---|
| Cr | chromium |
| Fe | iron |
| Co | cobalt |
| Ni | nickel |
| Cu | copper |
| Zn | zinc |
| As | arsenic |

TABLE 4-continued

| | |
|---|---|
| Se | selenium |
| Ag | silver |
| Cd | cadmium |
| Sb | antimony |
| Hg | mercury |
| Tl | thallium |
| Pb | lead |

Particularly preferred heavy metals for use in accordance with the invention are copper, cadmium and iron.

Without wishing to be bound by any theory, it is believed that elements such as those listed above, particularly those that have toxic effects, may accumulate in the epithelial cells that line renal tubules through which urine flows when it is being produced and adjusted by the kidney. In the event of AKI, those tubular epithelial cells may be damaged, and the accumulated elemental species thereby released into the urine. Elevated levels of the elements in question may therefore be indicative of AKI.

Thus, according to a first aspect of the invention, there is provided a method for diagnosing in a subject Acute Kidney Injury or a related or analogous disease state, which method comprises the steps of
  a) providing a sample taken from the subject;
  b) analysing the sample from the subject to determine the level of a biomarker selected from the atomic species listed in Table 1 above; and
  c) comparing the level of the biomarker in the sample to a reference level of the biomarker that is characteristic of a healthy subject, eg a subject having normal renal function;
  wherein an elevated level of the biomarker in the sample relative to the reference level is indicative of Acute Kidney Injury or a related or analogous disease state.

The method of the invention may be applied to a subject that displays symptoms of AKI or other disease state, or to a subject to which applies one or more risk factors associated with AKI or other disease state. Alternatively, in view of the prevalence of AKI in the hospitalised population, the method may be applied routinely for screening of all patients.

In a related aspect, the invention provides the use of an atomic species selected from those in Table 1 above as a biomarker for Acute Kidney Injury or a related or analogous disease state.

The invention further provides apparatus for use in diagnosing in a subject Acute Kidney Injury or a related or analogous disease state, which apparatus comprises an analytical element sensitive to the presence and/or concentration, in a sample taken from the subject, of a biomarker selected from the atomic species listed in Table 1 above.

The apparatus of the invention may also comprise means for receiving the sample or for otherwise bringing the sample into contact with the analytical element that is sensitive to the presence and/or concentration of the biomarker in the sample. The analytical element may comprise, without limitation, an optical waveguide or an electrochemical cell, or may be a test strip or dipstick or the like that, in use, is immersed in the sample.

The apparatus of the invention may also comprise means for comparing the level of the biomarker in the sample to a reference level of the biomarker that is characteristic of a healthy subject, eg a subject having normal renal function.

The apparatus of the invention may be configured as a Point-of-Care Test (POCT).

The invention further provides a test kit comprising an analytical element sensitive to the presence and/or concentration, in a sample taken from a subject, of a biomarker selected from the atomic species listed in Table 1 above, together with instructions for use of the analytical element in a method for diagnosing in a subject Acute Kidney Injury or a related or analogous disease state.

In all aspects of the invention, the biomarker may be one of the atomic species set out in Table 1, or in Table 2, or in Table 3, or in Table 4.

The use of the atomic species listed in Table 1 (or any of Tables 2 to 4) as biomarkers is advantageous in that the concentration of the biomarker is stable in the sample taken from the subject, as the biomarker is not subject to degradation as might be the case for a more complex organic biomarker. The analysis of the sample can be carried out accurately using appropriate analytical equipment, and for many such atomic species concentrations can be determined using equipment that is portable and/or simple enough for use by relatively untrained personnel at the point of care. Furthermore, the inventors' investigations indicate that levels of these species become elevated very soon after injury to the kidney, thereby providing a very early indication of AKI, leading to early intervention and optimisation of care, with corresponding clinical and economic benefits. The methods of the invention may be particularly beneficial in relation to older subjects, who are more likely to suffer AKI, as concentrations of the biomarkers in the kidneys of such subjects is likely to be greater than for younger subjects, due to a longer period of inadvertent environmental exposure to these atomic species, and hence greater accumulation.

The sample that is taken from the subject will most commonly be a sample of a bodily fluid, and may be a sample of any suitable bodily fluid, eg urine or blood. The sample may be used in the form in which it is obtained from the subject, or may be subjected to pre-treatment prior to analysis, eg dilution, concentration, fractionation, reaction with one or more chemical reagents, or other physical or chemical pre-treatment. For instance, a sample of whole blood may be fractionated, eg by plasmapheresis, and the analysis performed on an appropriate fraction, eg a sample of blood plasma. Other bodily fluids which may be sampled include bile, gastric fluid and vomit.

In other embodiments, the sample may be a solid or semi-solid sample, eg faeces or tissue.

Most conveniently, however, the sample is a sample of urine, and most preferably the urine sample is analysed without any physical or chemical pre-treatment.

The sample may be collected by conventional means. A urine sample may be collected in a standard urine cup or other vessel, with or without the use of urinary catheterisation. A blood sample may be collected by standard phlebotomy techniques.

The reference level with which the level of the biomarker in the sample is compared in the methods of the invention may be a standard reference level that is considered to be normal in the population in general, or in a subset of the population to which the subject belongs. Such a subset may be defined in terms of, for instance, gender, age, weight, body mass index, particular health parameters, or any combination of such characteristics. Standard reference levels may be established by routine measurement of the biomarkers in large groups of subjects, eg in all or some patients admitted to hospitals.

Alternatively, the reference level may be a baseline level measured in the subject prior to an event that may cause AKI. For instance, the reference level may be established by measuring the level of the biomarker before the subject undergoes a surgical procedure with the potential to cause AKI.

The level of the biomarker may be determined in a single measurement. For instance, a subject that is to undergo a surgical procedure may have the level of the biomarker measured prior to surgery and again a predetermined time after the surgical procedure. Alternatively, and more commonly, a series of measurements of the level of the biomarker are made, as a function of time. The timescale over which measurements are made, or the specific time at which a single measurement is made, will be determined by the typical behaviour of the level of the biomarker following an event that causes AKI. The inventors' investigations indicate that levels of the biomarker rise to a peak within 1 to 4 hours, and return to baseline values over a timescale of 12 to 48 hours. The methods of the invention thus typically comprise the analysis of a sample taken from the subject at a time within four hours of an event that may induce AKI, and more typically the analysis of samples taken from the subject at a plurality of times within four hours of such an event, and optionally one or more times greater than four hours. As noted above, the methods may also comprise the analysis of one or more samples taken from the subject prior to the event.

The methods of the invention may involve the measurement of the level of a single biomarker selected from the elemental species of Table 1 (or any of Tables 2 to 4), or the methods may involve the measurement of the levels of a panel of two or more such biomarkers. The methods of the invention may also involve the measurement of the level of at least one such biomarker and also the level of at least one other biomarker, for instance one or more known biomarkers for AKI such as NGAL, KIM-1, IL-18 or L-FABP.

Analysis of the sample may be carried out by any suitable analytical technique. One example is inductively coupled plasma mass spectrometry (ICP-MS), which is capable of detecting metals and certain non-metallic species at very low concentrations. This is achieved by ionising the sample with inductively coupled plasma and then using a mass spectrometer to separate and quantify the ionised species. The ions from the plasma are introduced into the mass spectrometer and separated on the basis of the mass-to-charge ratio. The detector of the mass spectrometer receives a signal that is proportional to the concentration of the atomic species in the sample.

ICP-MS may be used in combination with other techniques, such as high performance liquid chromatography (HPLC) or field flow fractionation (FFF).

ICP-MS has the capability to quantify more than one element simultaneously, and this technique may therefore offer particular benefits where more than one biomarker is used in a method of the invention, eg where a panel of biomarkers selected from the elemental species of Table 1 (or any of Tables 2 to 4) is used. In one embodiment, for instance, levels of two or more of cadmium, copper and iron may be measured.

Where only a single biomarker is used, however, other techniques may be feasible, notably atomic absorption techniques such as atomic absorption spectroscopy, in which the sample is atomised and the absorption of radiation, usually visible light, by the free atoms is used to quantify the concentration of the atomic species of interest.

Whilst analysis of the sample may be carried out using laboratory equipment and methodology such as that described above, such methods may not be available at all hospitals and/or may require specialised equipment and highly trained personnel. In general, it may therefore be preferable for the analysis to be carried out as a "Point-of-Care Test" (POCT), which can be performed by clinical personnel immediately after collection of a sample.

Apparatus and methods for the routine determination of certain of the atomic species of utility in the present invention are available, having previously been used in relation to, for instance, the determination of such species in domestic water supplies. Such apparatus and methods may be adapted for use in the methods of the present invention.

Concentrations of cadmium, for instance, can be measured by methods involving contacting of a sample with dithizone, which produces a pink to red colour that can be extracted with chloroform. Photometric measurement and comparison with a calibration curve prepared from standard cadmium solutions treated in the same manner as the sample may be used to derive the concentration of cadmium in the sample. In simple test kits, the analysis may involve merely visual comparison of a coloured solution, obtained by reaction of the sample with a reagent such as dithizone, with a colour chart.

Another technology that may be used in methods and apparatus according to the invention involves anodic or cathodic stripping voltammetry, which are voltammetric methods for quantitative determination of specific ionic species. In anodic stripping voltammetry, the analyte of interest is electroplated on a working electrode during a deposition step, and oxidized from the electrode during the stripping step. The current is measured during the stripping step. The oxidation of species is registered as a peak in the current signal at the potential at which the species begins to be oxidized.

Anodic stripping voltammetry equipment usually incorporates three electrodes: a working electrode, auxiliary electrode, and reference electrode. The solution being analyzed usually has an electrolyte added to it. For most standard tests, the working electrode is a bismuth or mercury film electrode. The mercury film forms an amalgam with the analyte of interest, which upon oxidation results in a sharp peak, improving resolution between analytes. The mercury film is formed over a glassy carbon electrode. In cases where the analyte of interest has an oxidizing potential above that of mercury, or where a mercury electrode would be otherwise unsuitable, a solid, inert metal such as silver, gold, or platinum may also be used.

Cathodic stripping voltammetry is similar to anodic stripping voltammetry, save that, for the plating step, the potential is held at an oxidizing potential, and the oxidized species are stripped from the electrode by sweeping the potential positively.

In other embodiments, the analysis may be carried out using a biosensor. Such a system typically includes a sample cell having a surface that is sensitive to the presence of the biomarker that is to be detected. For instance, the surface may be coated with biomolecules bound to ligands that bind competitively with the biomarker, such that the ligands dissociate from the surface if, and to the extent that, the ligand is present in the sample. If the ligands are labelled, eg with a fluorescent label, then the dissociation of the ligand from the surface can be detected and quantified.

By way of example, DNA-based sensors may be used to detect metal ions by virtue of the ability of certain metal ions to bind selectively to some nucleotide bases to form stable metal-mediated DNA duplexes. For instance, mercury ions are able to coordinate thymine (T) bases selectively to form stable T-Hg-T complexes, and silver ions interact specifically with cytosine-cytosine (C-C) mismatches. Detectors for lead are also known, based on the Pb-dependent DNAzyme and the Pb-stabilised G-quadruplex. Structure-switching DNA biosensors for the detection of various metal ions have been proposed, using various detection methods including fluorescence, surface-enhanced Raman spectroscopy, resonance scattering, colorimetry, electrochemical methods, and evanescent wave optical techniques. In such biosensors, structure-switching is induced by the formation of weak non-covalent bonds, which is generally specific to the interaction of interest and is unaffected by other species present in the sample. The switching occurs rapidly so that such devices are suitable for immediate in situ (POCT) monitoring of specific targets.

In one form of apparatus that may be suitable for carrying out methods of the invention, an evanescent wave optical biosensor is used. When light propagates through an optical fibre or waveguide by total internal reflection, a rapidly decaying electromagnetic field or evanescent wave is generated. The evanescent wave decays exponentially from the interface, with a typical penetration depth of the order of 100 nm. The evanescent wave can excite fluorescence in fluorophores located within it, but the limited depth of the evanescent wave allows for differentiation between fluorophores that are bound to the interface, within the evanescent wave, and those that are unbound, in the bulk sample. Thus, to measure mercury in a sample, short DNA probes that are complementary to fluorescently-labelled cDNA containing a T-T mismatch structure can be immobilised onto the surface of an optical fibre waveguide. Fluorescently-labelled cDNA can then be bound to the DNA probes on the surface. When the surface is then brought into contact with a sample containing mercury ions, some of the fluorescently-labelled cDNA binds to the mercury ions and dehybridises from the probes immobilised on the surface. This leads to a reduction in the fluorescence signal, the reduction being proportional to the concentration of mercury.

Analogous methodologies may be used for the determination of other biomarkers according to the invention.

The biomarkers of the present invention are believed to be reliable, sensitive and specific biomarkers for AKI. As such, there is the potential for the frequent and widespread use of the methods of the present invention in acute hospitals internationally. Any patient at risk of AKI could be screened with one or more such tests. Specific risk factors for AKI include: older age (eg >65 years), CKD, previous AKI, liver disease, heart failure, sepsis, haematological malignancy, neurological impairment. Consequently, patients admitted unwell, with any of these risk factors, might be screened with the biomarker assay. Similarly, patients undergoing any of the following procedures might be screened to identify those at risk of subsequently developing AKI:

Major surgery, including without limitation cardiac surgery;
Coronary angiogram or angioplasty;
Radiological investigations requiring injection of contrast agents (risk of "contrast agent-induced AKI");
Trauma;
Burns;
Chemotherapy.

The methods of the invention may also be utility in the routine screening of any patients admitted to intensive care or coronary care units. Similarly, as AKI can occur after pregnancy, the biomarkers may be measured routinely ante- and post-natally in maternity units.

Apart from screening for AKI, the methods of the invention may be used in connection with renal transplantation, which involves a significant ischaemic insult to the transplanted kidney, especially when there is a deceased donor kidney, but also for live donor kidneys. The kidney is often slow to start working after implantation into the recipient ("delayed graft function"), or works initially but then develops the equivalent of AKI after a few days. The biomarkers of the invention may be elevated in a urine sample taken from a prospective donor prior to harvesting of a kidney for transplantation, and this may be indicative of a risk of delayed graft function. Similarly, the biomarkers of the invention may be elevated in the urine of the recipient (if they pass urine), which might allow estimation of the risk of the transplanted kidney developing the equivalent of AKI. This information may be useful in various ways, including deciding on when to discharge the patient, whether to undertake renal biopsy, and/or whether to change immunosuppression drugs.

In addition to the above, the methods of the present invention may be useful in relation to acute liver damage. It is known that the liver also accumulates cadmium, and it is therefore possible that, in acute liver damage (drug toxicity, hepatitis), cadmium levels in blood might rise.

Although the subject is most likely to be a human subject, it is to be expected that the atomic species of Table 1 (or any of Tables 2 to 4) will be biomarkers of AKI in other mammals. Thus, the methods of the invention may have utility in the veterinary field.

The invention will now be illustrated, by way of example only, with reference to the accompanying Figures.

CLINICAL PROTOCOL

A pig model of AKI was developed. The pig is an excellent model for human kidney disease because the anatomy and physiology of pig and human kidneys are similar.

The pigs are anaesthetised for general surgery, intubated and subjected to a midline laparotomy to reveal the right and left kidneys, which are each fully clamped for variable times (20-180 minutes), after which the clamps are removed and the incision site closed. A bladder catheter (12 Fr) is inserted for urine collection, and the pigs are recovered to a pen.

The model thus involves clamping the renal artery for a defined time (up to 180 minutes), and then reperfusing to cause an Ischaemia-Reperfusion (IR)-induced injury, which is an extreme type of insult to the kidney.

Urine samples are collected before clamping of the renal artery (baseline), immediately after reperfusion (t=0), and at various time intervals thereafter (up to 48 hrs).

The concentration of various biomarkers in the urine samples is measured by ICP-MS.

Concentration of Urinary Cadmium

Figure 1A:
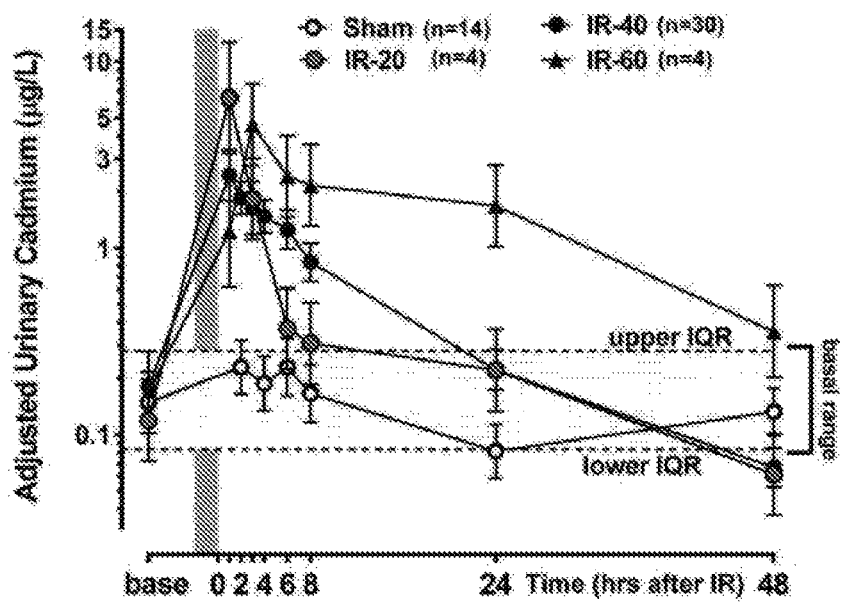
FIG. 1a shows the change in urinary cadmium (normalised to creatinine levels) with time in a pig of similar weight to an adult human (50-70 kg), after inducing a known degree of kidney injury (Ischaemia-Reperfusion (IR)-induced injury at time zero).

FIG. 1a shows (on a logarithmic scale) the concentration of cadmium in the urine of the pigs prior to, and at several time points after, various degrees of IR-induced injury to the kidney, the degree of injury being dependent on the duration of clamping of the renal artery (20, 40 or 60 minutes). As a control, measurements were also made for pigs that underwent surgery but without clamping of the renal artery to induce injury to the kidney ("Sham").

It can be seen that the baseline (pre-injury) concentrations of cadmium for each group of subjects was similar, and for the Sham group the concentration of cadmium remained within the basal range.

For the pigs that suffered injury to the kidney, an increase in cadmium concentration was observed, the magnitude of the increase being proportional to the duration of clamping of the renal artery, and hence the severity of the injury. The time taken for the concentration of cadmium to return to the basal range is also shown to be proportional to the duration of clamping of the renal artery, and hence the severity of the injury (return to baseline was approximately 6 hours, 24 hours and 48 hours for IR-20, IR-40 and IR-60 respectively).

The results indicate that urinary cadmium is an excellent, early (within the first 24 hours post-injury) biomarker of AKI.

Figure 1B:
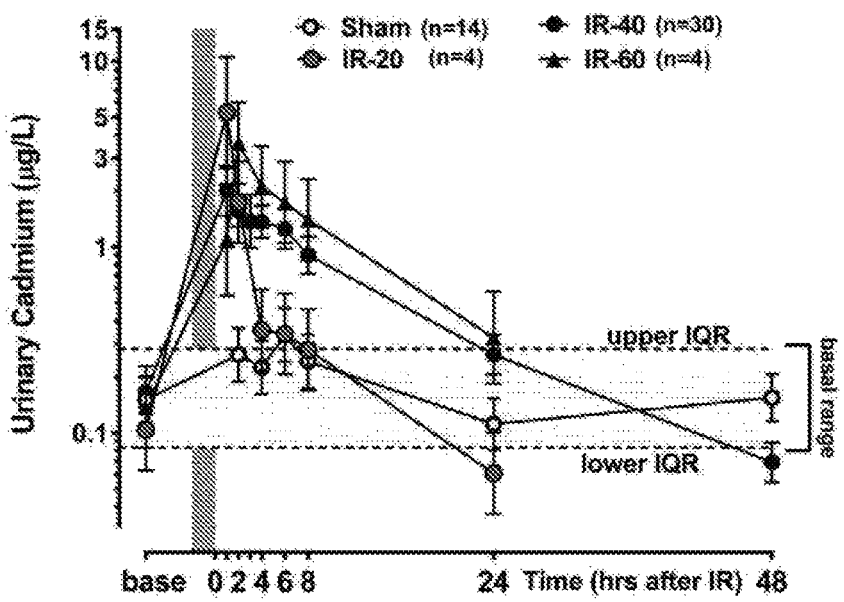
FIG. 1b is similar to FIG. 1a, but with the data shown without normalisation to creatinine levels.
Figure 2A:
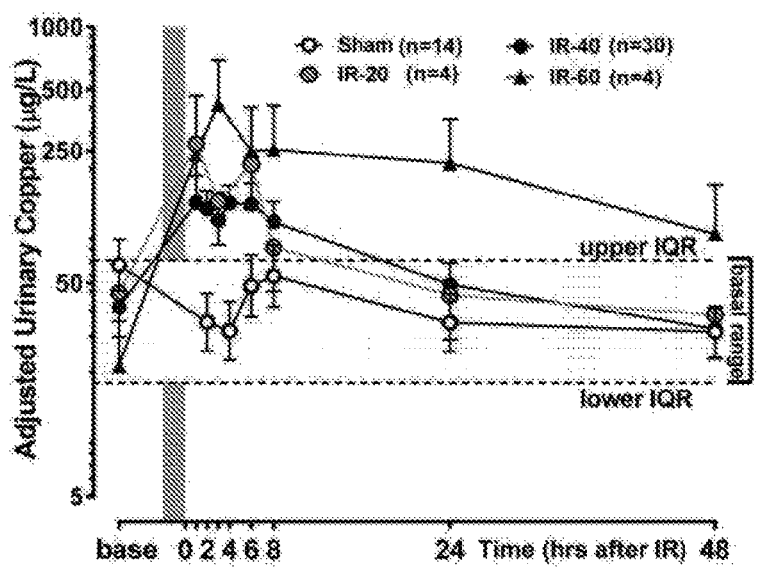
FIG. 2a shows the change in urinary copper (normalised to creatinine levels) with time in a pig of similar weight to an adult human (50-70 kg), after inducing a known degree of kidney injury (Ischaemia-Reperfusion (IR)-induced injury at time zero).
Figure 2B:
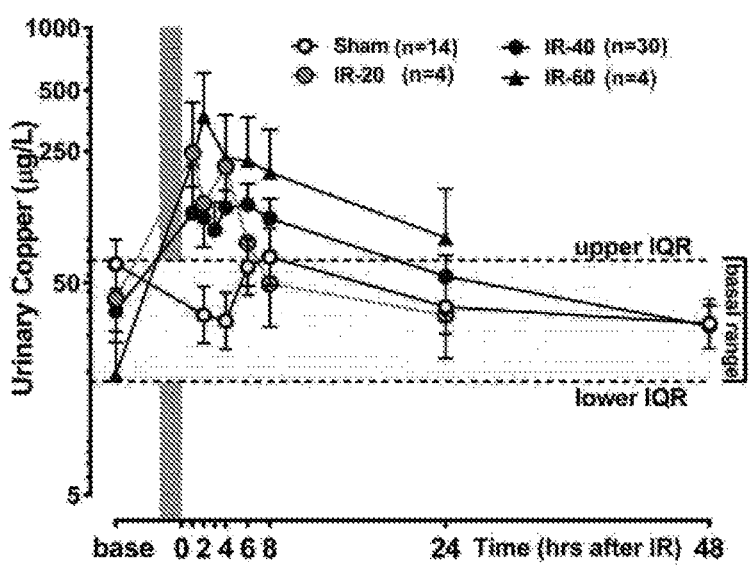
FIG. 2b is similar to FIG. 2a, but with the data shown without normalisation to creatinine levels.
Figure 3A:
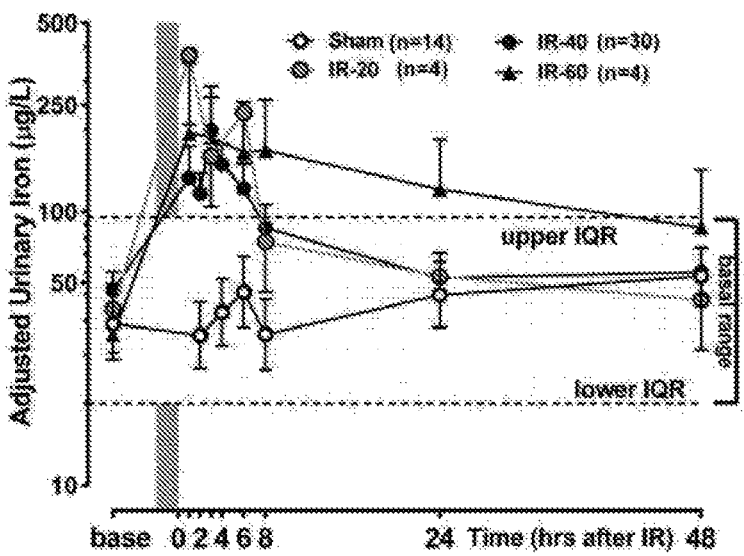
FIG. 3a shows the change in urinary iron with time in a pig of similar weight to an adult human (50-70 kg), after inducing a known degree of kidney injury (Ischaemia-Reperfusion (IR)-induced injury at time zero).
Figure 3B:
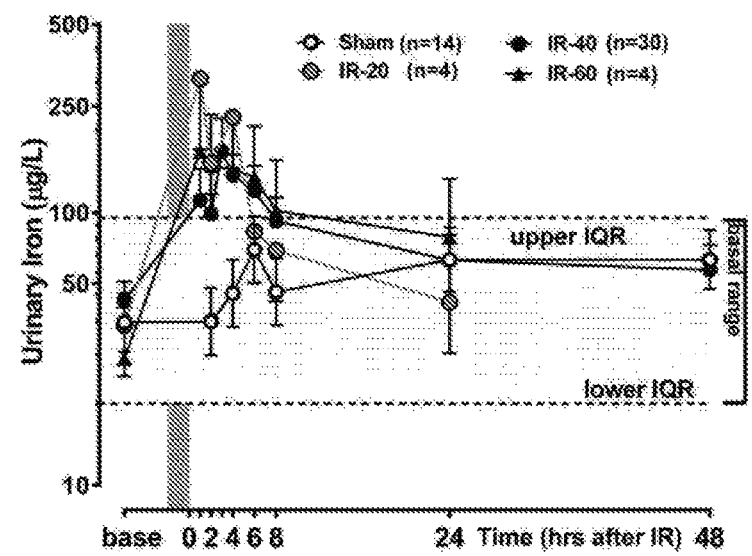
FIG. 3b is similar to FIG. 3a, but with the data shown without normalisation to creatinine levels.

In FIG. 1a, the concentration of cadmium is adjusted to urine creatinine (14,256 µmol/L), to compensate for possible variations due to large differences in volume of urine passed by different subjects. However, data not adjusted for creatinine in that way is shown in FIG. 1b; it can be seen that the observed behaviour is qualitatively very similar to that depicted in FIG. 1a.

Concentration of Urinary Copper and Urinary Iron

FIGS. 2a and 2b, and 3a and 3b show data similar to FIG. 1, but for copper and iron (respectively), rather than cadmium.

The observed results are qualitatively very similar to those for cadmium (FIGS. 1a and 1b), with a marked increase in urinary copper and iron post-injury.

The results indicate that urinary copper and urinary iron are excellent, early (within the first 24 hours post-injury) biomarkers of AKI.

Receiver-Operating-Characteristic Curves

A Receiver-Operating-Characteristic (ROC) curve is a graphical plot that illustrates the performance of a binary classifier system as its discrimination threshold is varied. The curve is created by plotting the true positive rate (sensitivity) against the false positive rate at various threshold settings.

Figure 4:
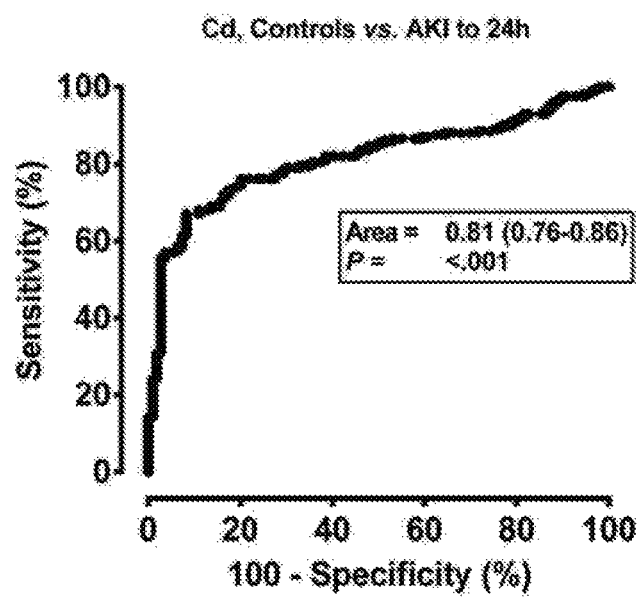
FIG. 4 is a Receiver-Operating-Characteristic (ROC) curve for urinary cadmium as a marker of AKI.
Figure 5:
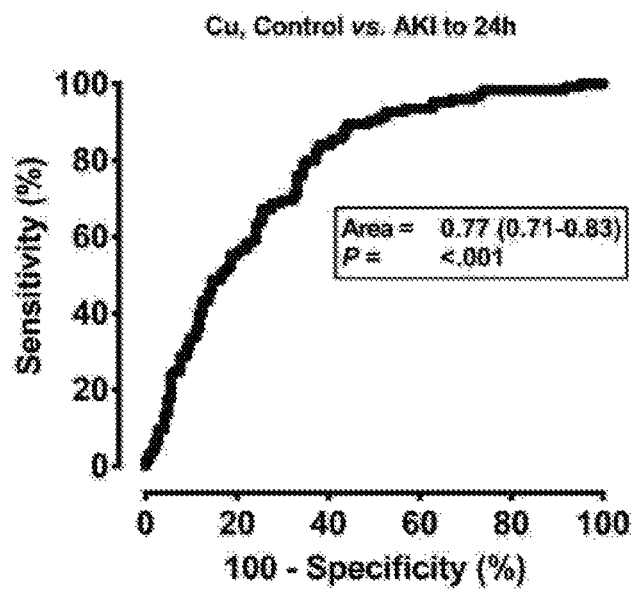
FIG. 5 is a Receiver-Operating-Characteristic (ROC) curve for urinary copper as a marker of AKI.
Figure 6:
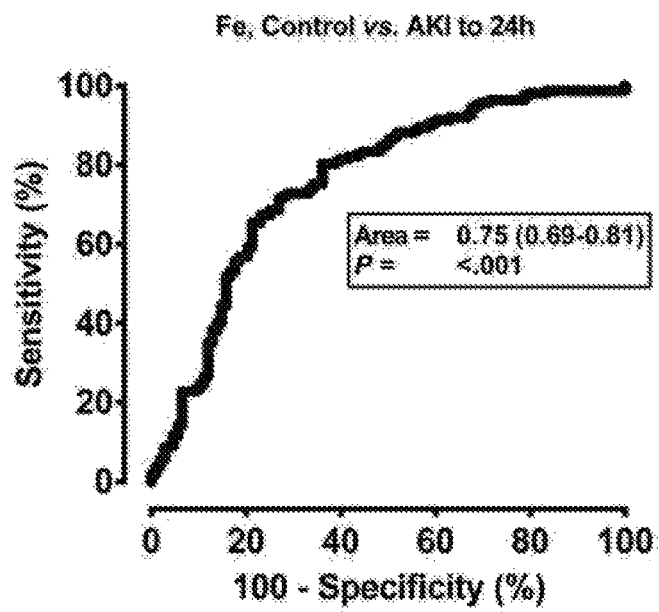
FIG. 6 is a Receiver-Operating-Characteristic (ROC) curve for urinary iron as a marker of AKI.

FIGS. 4, 5 and 6 show ROC curves for all data generated in relation to controls and IR-induced injury subjects for cadmium (FIG. 4), copper (FIG. 5) and iron (FIG. 6). The area under the curve (AUC) is a measure of the reliability of the test in identifying individuals with or without the disease state under consideration, ie AKI. An AUC of 0.75 or greater is an indication that the test is very good.

For cadmium, the AUC was 0.81, with a 95% confidence interval of 0.76-0.86.

For copper, the AUC was 0.77, with a 95% confidence interval of 0.71-0.83.

For iron, the AUC was 0.75, with a 95% confidence interval of 0.69-0.81.

Thus, cadmium, copper and iron are indicated to be very good biomarkers for AKI.

Cut-Off for Positive Prediction of Disease

Plotting the ROC-derived estimates for sensitivity (left y-axis) and specificity (right y-axis) against urinary biomarker concentration (x-axis on a $\log_{10}$ scale) indicates the cut-off for positive prediction of AKI with >80% confidence based upon spot-measurement of the urinary biomarker.

Figure 7:
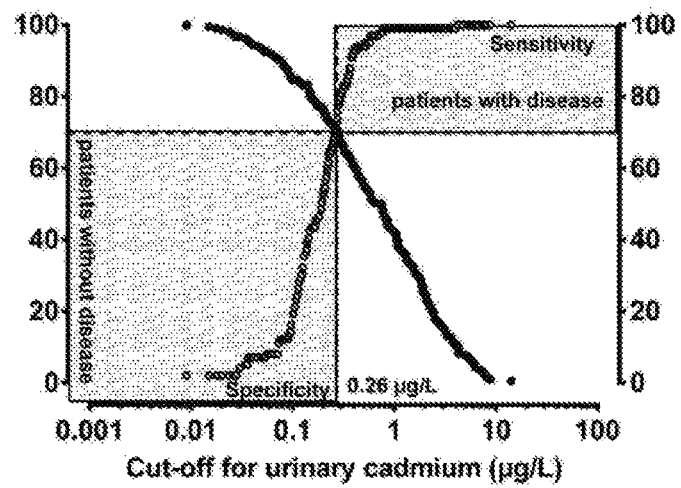
FIG. 7 is a plot of the ROC-derived estimates for sensitivity (left y-axis) and specificity (right y-axis) against urinary cadmium (x-axis on a $\log_{10}$ scale), indicating the cut-off for positive prediction of disease.

Thus, FIG. 7 is a plot of the ROC-derived estimates for sensitivity (left y-axis) and specificity (right y-axis) against urinary cadmium (x-axis on a $\log_{10}$ scale) and it indicates that the cut-off for positive prediction of AKI with >80% confidence based upon spot-measurement of urinary cadmium is >0.26 µg/L.

Figure 8:
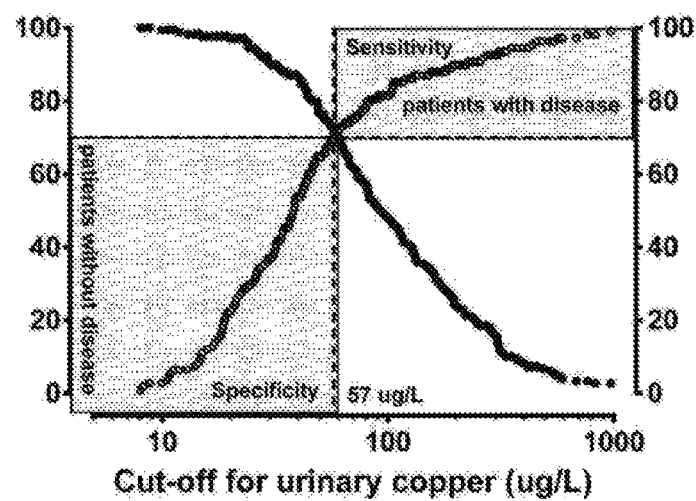
FIG. 8 is a plot of the ROC-derived estimates for sensitivity (left y-axis) and specificity (right y-axis) against urinary copper (x-axis on a $\log_{10}$ scale), indicating the cut-off for positive prediction of disease.
Figure 9:
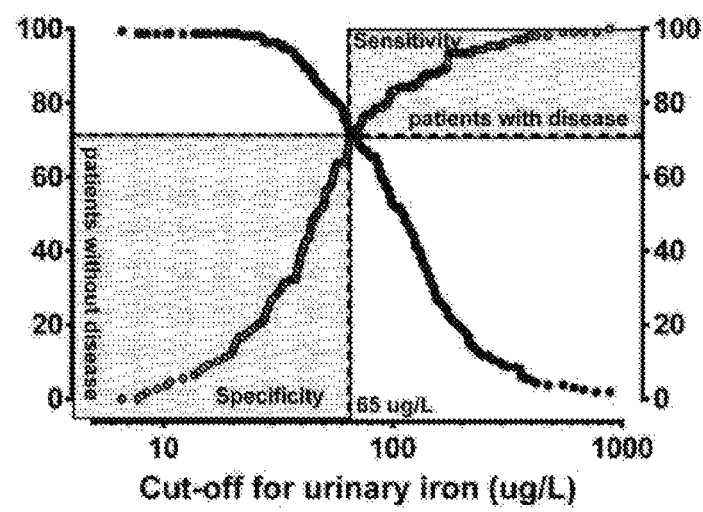
FIG. 9 is a plot of the ROC-derived estimates for sensitivity (left y-axis) and specificity (right y-axis) against urinary iron (x-axis on a $\log_{10}$ scale), indicating the cut-off for positive prediction of disease.

FIGS. 8 and 9 are the same plots for copper and iron respectively.

The cut-offs indicated for positive prediction of acute disease are >57 µg/L for copper and >65 µg/L for iron.

Concentration of Various Elements in Porcine and Rat Kidneys

The elemental composition of kidney tissue was measured for young healthy pigs (n=20), aged healthy pigs (n=8) and, for comparison purposes, young healthy laboratory rats (n=12). Major and trace elements were measured in a known mass of freeze-dried tissue after nitric acid hydrolysis using inductively-coupled plasma mass spectrometry (ICP-MS). Mean concentrations ±1 S.D. are shown in Table 5 below, expressed in µg/g dry matter (DM). The young pigs were 3-4 months old, the aged pigs were 5-6 years of age and the young rats (Wistar) were 10-12 weeks of age. All pigs were mixed-breed (landrace/large white/duroc) commercial stock.

TABLE 5

|  | Young Pigs | Aged Pigs | Young rats | P-value for age in pigs |
|---|---|---|---|---|
| Major element (µg/g DM) | | | | |
| Sodium | 7373 ± 1971 | 5634 ± 1165 | 6710 ± 703 | 0.03 |
| Potassium | 11814 ± 2547 | 10143 ± 2509 | 12012 ± 1143 | 0.14 |

TABLE 5-continued

|  | Young Pigs | Aged Pigs | Young rats | P-value for age in pigs |
|---|---|---|---|---|
| Calcium | 384 ± 256 | 597 ± 95 | 258 ± 42 | 0.04 |
| Magnesium | 790 ± 179 | 883 ± 267 | 859 ± 79 | 0.30 |
| Phosphorus | 15163 ± 3892 | 12304 ± 1186 | 12438 ± 993 | 0.08 |
| Sulphur | 10119 ± 1981 | 15364 ± 6366 | 6229 ± 828 | 0.04 |
| Total ME | 45301 ± 10269 | 44928 ± 9410 | 38511 ± 3458 | — |
| Trace element (µg/g DM) |  |  |  |  |
| Iron | 170 ± 103 | 354 ± 48 | 329 ± 44 | <.001 |
| Zinc | 155 ± 56 | 147 ± 22 | 97.2 ± 7.14 | 0.72 |
| Copper | 33.5 ± 14.3 | 49.7 ± 8.4 | 27.4 ± 3.0 | 0.009 |
| Rubidium | 16.2 ± 4.9 | 14.7 ± 3.7 | 20.9 ± 1.5 | 0.53 |
| Aluminium | nd | nd | 10.95 ± 5.53 | — |
| Selenium | 7.51 ± 1.54 | 13.8 ± 3.9 | 4.99 ± 0.38 | <.001 |
| Manganese | 6.72 ± 2.06 | 8.29 ± 1.40 | 3.41 ± 0.48 | 0.07 |
| Molybdenum | 2.90 ± 0.95 | 2.99 ± 0.23 | 1.15 ± 0.14 | 0.27 |
| Chromium | 3.55 ± 1.79 | 3.32 ± 0.43 | 0.17 ± 0.23 | 0.27 |
| Cadmium | 1.47 ± 0.53 | 3.17 ± 0.79 | 0.02 ± 0.00 | <.001 |
| Barium | nd | nd | 0.09 ± 0.03 | — |
| Strontium | nd | nd | 0.05 ± 0.05 | — |
| Cobalt | 0.05 ± 0.02 | 0.09 ± 0.04 | 1.19 ± 0.09 | 0.004 |
| Caesium | 0.05 ± 0.03 | 0.06 ± 0.02 | 0.12 ± 0.012 | 0.83 |
| Vanadium | 0.07 ± 0.06 | 0.04 ± 0.03 | 0.03 ± 0.009 | 0.13 |
| Thallium | nd | nd | 0.04 ± 0.006 | — |
| Total TE | 363 ± 19 | 597 ± 62 | 499 ± 50 |  |

The elemental composition is shown to be broadly similar for young and aged pigs and young laboratory rats. However, of note, and in agreement with published literature from cadaveric material, the concentration of cadmium, copper and iron increases with age, reinforcing the notion of bioaccumulation of these elements in the main route of elimination for water-soluble toxins and metabolic wastes.

Figure 10:
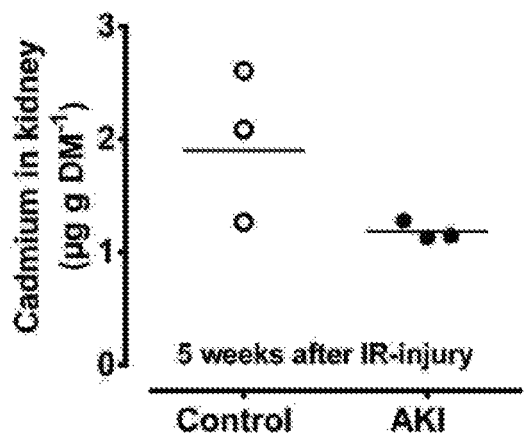
FIG. 10 shows the concentration of cadmium (top panel), copper (middle panel) and iron (lower panel) in porcine kidneys measured at 5 weeks post IR-injury.
Figure 10:
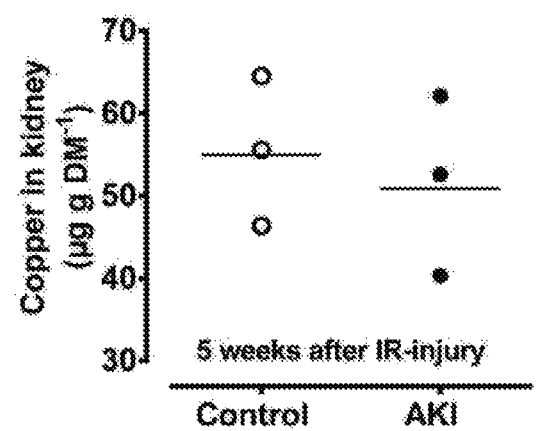
Figure 10:
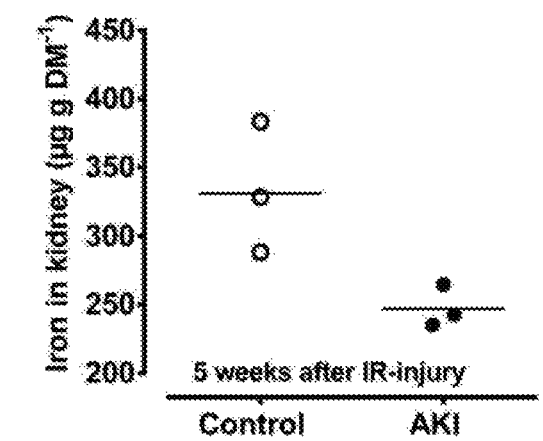

FIG. 10 shows the results of an additional study in which the concentration of cadmium, copper and iron in porcine kidneys was measured at 5 weeks post IR-injury (Control, n=3; IR-AKI, n=3). Data is presented as a dot-plot (line at geometric mean) of the concentration in µg/g dry matter (DM). All graphs and ROC curve statistics were generated in Graphpad Prism 6 (Graphpad Software Inc, Ca, USA). Quantitative time-series data were analysed by REML with treatment (Control vs. IR) as a fixed effect and time as a within-animal repeated measure (Genstat v16, Rothampsted, UK). Elemental data were $\log_{10}$ transformed prior to analysis. Statistical significance was accepted at $P<0.05$.

The kidney tissue concentration of cadmium and iron in particular had depleted, consistent with loss of proximal tubular epithelial cells that specifically accumulate these elements in highest concentration. It is hypothesised that the results for copper may be distorted by the copper content in drinking water and/or food, and some degree of variability in iron concentrations in kidney tissue may be expected for the same reason.

Concentration of Urinary Cadmium, Copper and Iron in Healthy Volunteers

Major and trace elements were measured in spot-samples of urine from young, healthy male and female volunteers (n=12 males, n=12 females), and for comparison catheterised but healthy pigs (n=24-53, baseline urine sample), by inductively-coupled plasma mass spectrometry (ICP-MS). The results shown in Table 6 below are median concentration values ($1^{st}$ and $3^{rd}$ interquartile range (IQR)). The young pigs were 3-4 months old (50-60 kg). The data were compared by one-way ANOVA, with urinary creatinine as a co-variate.

TABLE 6

|  | Human (female) | Human (male) | Pigs (female) | P-value (humans) |
|---|---|---|---|---|
| Major element (mg/L) |  |  |  |  |
| Potassium | 1751 (1101, 3850) | 3145 (1549, 3850) | 1681 (794, 2654) | 0.51 |
| Sodium | 765 (260, 2330) | 1841 (871, 2330) | 625 (324, 1002) | 0.58 |
| Phosphorus | 340 (191, 873) | 691 (288, 1122) | 16.4 (8.9, 95) | 0.94 |
| Sulphur | 304 (191, 873) | 715 (344, 873) | 422 (208, 570) | 0.32 |
| Calcium | 49.5 (35.9, 146) | 100 (58, 146) | 68.8 (22.4, 182) | 0.43 |
| Magnesium | 42.5 (20.2, 109) | 61.5 (34.4, 109) | 76.6 (51.3, 135) | 0.25 |
| Boron | 0.99 (0.60, 1.74) | 1.04 (0.61, 1.74) | 0.89 (0.48, 1.12) | 0.67 |
| Total major elements | 3073 (2324, 9168) | 6203 (2863, 9168) | 2627 (1541, 4145) | 0.10 |
| Trace element (µg/L) |  |  |  |  |
| Rubidium | 1188 (827, 2295) | 1912 (1282, 2295) | 661 (459, 1238) | 0.27 |
| Zinc | 134 (83, 505) | 341 (180, 505) | 348 (204, 688) | 0.23 |
| Strontium | 72.5 (46.3, 195) | 118 (44, 195) | 157 (80, 270) | 0.26 |
| Molybdenum | 24.0 (13.0, 73.0) | 47.7 (22.9, 73.0) | 56.7 (39.1, 109) | 0.38 |
| Aluminium | 42.4 (37.3, 46.1) | 44.5 (42.6, 46.1) | 12.3 (6.1, 33.8) | 0.76 |
| Iron | 32.2 (31.6, 37.8) | 35.4 (34.2, 37.8) | 39.3 (20.8, 95.8) | 0.95 |
| Selenium | 20.3 (7.7, 37.7) | 26.7 (16.4, 37.7) | 68.0 (36.8, 99.1) | 0.41 |
| Lithium | 16.8 (10.7, 26.9) | 18.6 (13.3, 26.9) | — | 0.67 |
| Copper | 15.0 (13.9, 19.1) | 18.5 (14.6, 19.1) | 35.5 (18.1, 69.1) | 0.67 |
| Arsenic | 9.00 (4.41, 35.8) | 25.4 (11.6, 35.8) | 1.55 (0.94, 2.46) | 0.30 |
| Caesium | 5.30 (3.06, 10.00) | 7.17 (6.07, 10.00) | 1.75 (1.05, 2.54) | 0.52 |
| Nickel | 5.65 (5.20, 6.31) | 5.96 (5.27, 6.31) | 9.76 (3.23, 16.9) | 0.92 |
| Chromium | 5.29 (5.19, 5.63) | 5.42 (5.25, 5.63) | 1.32 (0.62, 2.10) | 0.31 |
| Barium | 2.30 (1.60, 3.80) | 2.09 (1.78, 3.80) | 13.9 (7.8, 17.3) | 0.39 |
| Manganese | 1.14 (1.06, 1.25) | 1.17 (1.14, 1.25) | 3.50 (1.32, 6.72) | 0.44 |
| Lead | 0.92 (0.84, 1.15) | 0.97 (0.90, 1.15) | 1.16 (0.72, 2.41) | 0.56 |
| Vanadium | 0.37 (0.30, 0.91) | 0.57 (0.31, 0.91) | 0.77 (0.50, 1.34) | 0.26 |
| Cadmium | 0.20 (0.16, 0.33) | 0.21 (0.14, 0.33) | 0.14 (0.08, 0.28) | 0.41 |
| Cobalt | 0.30 (0.19, 0.32) | 0.23 (0.18, 0.32) | 1.17 (0.76, 2.83) | 0.63 |

TABLE 6-continued

|  | Human (female) | Human (male) | Pigs (female) | P-value (humans) |
|---|---|---|---|---|
| Thallium | 0.18 (0.12, 0.39) | 0.28 (0.12, 0.39) | — | 0.30 |
| Beryllium | 0.01 (0.01, 0.02) | 0.01 (0.01, 0.02) | nd | 0.50 |
| Osmolality (Osm/L) | 251 (179, 734) | 462 (248, 734) | 417 (362, 490) | 0.28 |
| Creatinine (μmol/L) | 3301 (2575, 14424) | 9821 (4199, 14424) | 8617 (5425, 11684) | 0.01 |
| Total trace elements | 1622 (1202, 3182) | 2699 (1831, 3182) | 1800 (1287, 3212) | 0.15 |

The concentrations of urinary cadmium, copper and iron are similar between young healthy male and female volunteers and below all cut-offs established from the preclinical animal (porcine) model (for reference see FIGS. 7-9). The urinary trace element profile obtained from the cohort of pigs was also broadly similar, with any differences likely reflecting differences in dietary sources (eg low aluminium, high selenium).

Figure 11:
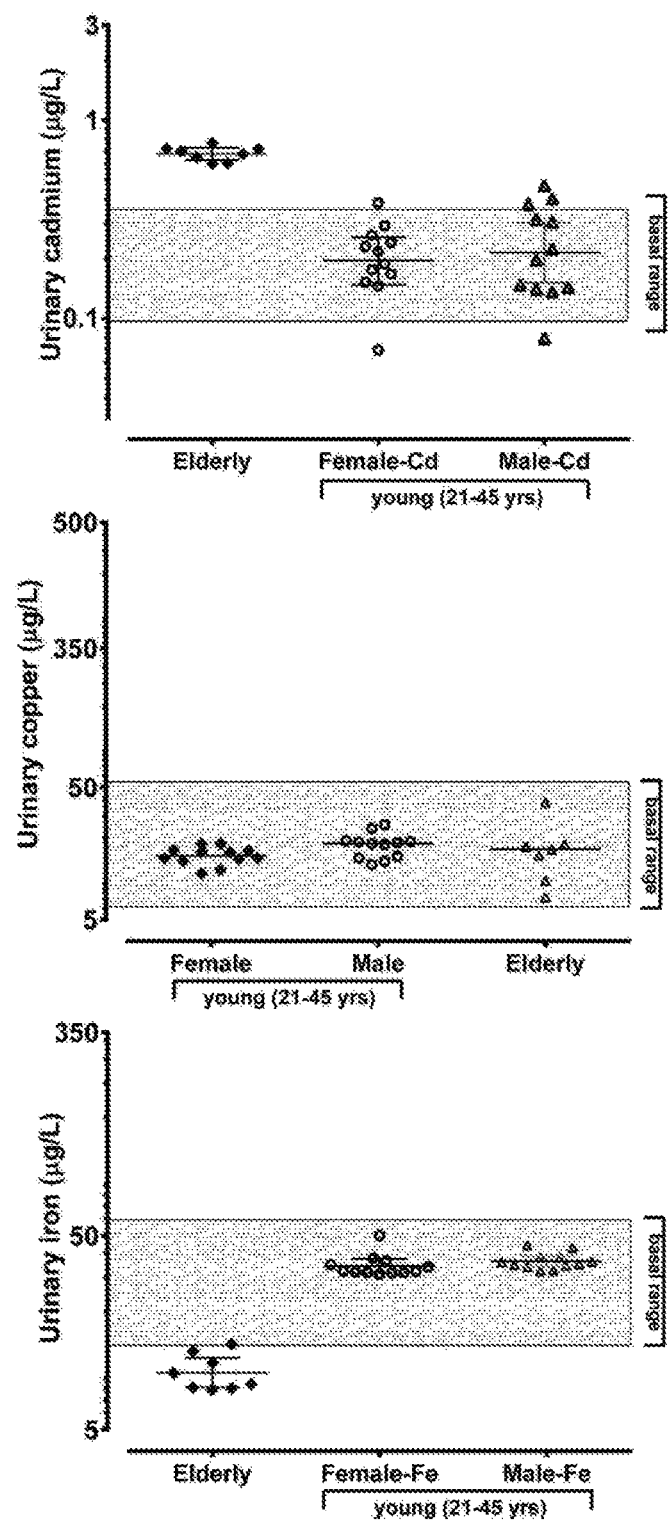
FIG. 11 shows baseline levels of urinary cadmium (top panel), copper (middle panel) and iron (lower panel) in elderly, healthy volunteers.

The urinary trace element profiles of elderly 65 years of age), healthy male and female volunteers were also measured and were also below all cut-offs established from the preclinical animal (porcine) model, with the exception of an increase in baseline cadmium. The results for cadmium, copper and iron are shown in FIG. 11. Elements were determined in spot-samples by inductively-coupled plasma mass spectrometry (ICP-MS). The basal range (horizontal shaded area) was determined from summary statistics ($1^{st}$ and $3^{rd}$ quartile) of all baseline determinations for each element. Graphs were generated in Graphpad Prism 6 (Graphpad Software Inc, Ca, USA).

The invention claimed is:

1. An analytical method for diagnosing in a subject Acute Kidney Injury (AKI) or a related or analogous disease state, the method comprising the steps of
   a) providing a sample taken from the subject;
   b) analysing the sample from the subject to determine the level of a biomarker selected from the group consisting of aluminum, silicon, phosphorous, sulfur, chlorine, scandium, titanium, vanadium, chromium, manganese, cobalt, nickel, copper, zinc, gallium, germanium, arsenic, selenium, bromine, yttrium, zirconium, niobium, molybdenum, technetium, ruthenium, rhodium, palladium, silver, cadmium, indium, tin, antimony, tellurium, iodine, hafnium, tantalum, tungsten, rhenium, osmium, iridium, platinum, gold, mercury, thallium, lead, bismuth, polonium, astatine, flerovium, livermorium, lanthanum, cerium, praseodymium, neodymium, promethium, samarium, europium, gadolinium, terbium, dysprosium, holmium, erbium, thalium, ytterbium, lutetium, actinium, thorium, protactinium, uranium, neptunium, plutonium, americium, curium, berkelium, californium, einsteinium, fermium, mendelevium, nobelium, lawrencium, or combinations thereof, wherein said analysing comprises introducing the sample into an voltammetric cell and operating the voltammetric cell while the sample contacts surfaces of electrodes of the voltammetric cell by applying sufficient potential across electrodes to elicit a redox reaction of the biomarker on a working electrode, and measuring the resulting current to obtain a quantified level for one of said biomarkers in the sample;
   c) comparing the level of the biomarker in the sample to a reference level of the biomarker that is characteristic of a subject having normal renal function; and
   d) assigning the subject as having Acute Kidney Injury or a related or analogous disease state based on an elevated level of one of said biomarkers in the sample relative to the reference level.

2. The method according to claim 1 in which the biomarker is cadmium, copper, or zinc.

3. The method according to claim 1 in which the sample is a urine sample or a blood sample.

4. The method according to claim 1 in which the reference level with which the level of the biomarker in the sample is compared is a standard reference level that is considered to be normal in the population in general, or in a subset of the population to which the subject belongs.

5. The method according to claim 1 in which the reference level with which the level of the biomarker in the sample is compared is a baseline level measured in the subject prior to an event that may cause AKI or a related or analogous disease state.

6. The method according to claim 1 in which the level of the biomarker is determined in a single measurement.

7. The method according to claim 1 in which a series of measurements of the level of the biomarker are made, as a function of time.

8. The method according to claim 7, wherein measurements are made on a sample taken from the subject at a time within four hours of an event that may induce AKI, and optionally one or more times greater than four hours.

9. The method according to claim 8, further comprising the analysis of one or more samples taken from the subject prior to the event.

10. The method according to claim 1 which involves the measurement of the level of exactly one of said biomarkers.

11. The method according to claim 1 which involves the measurement of the levels of a panel of two or more of said biomarkers.

12. The method according to claim 10, which also involves the measurement of the level of at least one other biomarker for AKI selected from the group of NGAL, MM-1, IL-18, and L-FABP.

13. The method according to claim 1 wherein said analysingjs carried out by operating the voltammetric cell using anodic or cathodic stripping voltammetry.

14. The method according to claim 1 which is used to diagnose Acute Kidney Injury, injury to a transplanted kidney, or acute liver damage.

* * * * *

UNITED STATES PATENT AND TRADEMARK OFFICE
CERTIFICATE OF CORRECTION

PATENT NO. : 10,761,103 B2  
APPLICATION NO. : 15/541980  
DATED : September 1, 2020  
INVENTOR(S) : Mark Devonald and David Gardner Page 1 of 1

It is certified that error appears in the above-identified patent and that said Letters Patent is hereby corrected as shown below:

In the Claims

In Claim 12, at Column 16, Line 54, delete "MM-1" and insert --KIM-1--; and

In Claim 13, at Column 16, Lines 55-56, delete "analysingis" and insert --analysing is--.

Signed and Sealed this  
First Day of December, 2020

Andrei Iancu  
*Director of the United States Patent and Trademark Office*